United States Patent [19]

Maruyama et al.

[11] 4,080,328
[45] Mar. 21, 1978

[54] N-SUBSTITUTED HETEROCYCLIC DERIVATIVES AND PREPARATION THEREOF

[75] Inventors: Isamu Maruyama, Minoo; Masaru Nakao; Kikuo Sasajima, both of Toyonaka; Shigeho Inaba, Takarazuka; Izumi Yanagihara, Osaka; Hisao Yamamoto, Nishinomiya, all of Japan

[73] Assignee: Sumitomo Chemical Company, Limited, Osaka, Japan

[21] Appl. No.: 484,274

[22] Filed: Jun. 28, 1974

Related U.S. Application Data

[63] Continuation of Ser. No. 269,921, Jul. 10, 1972, abandoned.

[30] Foreign Application Priority Data

Jul. 13, 1971    Japan .................................. 46-52221

[51] Int. Cl.² ............................................ C07D 401/04
[52] U.S. Cl. ............................ 260/293.6; 260/293.66; 424/267
[58] Field of Search ...................................... 260/293.6

[56] References Cited

U.S. PATENT DOCUMENTS

| 3,196,157 | 7/1965  | Janssen ............... | 260/294   |
| 3,225,052 | 12/1965 | Janssen ............... | 260/293.4 |
| 3,238,216 | 3/1966  | Janssen ............... | 260/293.4 |
| 3,818,017 | 6/1974  | Janssen et al. ....... | 260/293.6 |
| 3,894,030 | 7/1975  | Janssen et al. ....... | 260/293.6 |

FOREIGN PATENT DOCUMENTS

| 663,431   | 11/1965 | Belgium ............... | 260/293.6 |
| 794,351   | 9/1968  | Canada ................ | 260/293.6 |
| 3,043     | 1/1965  | France ................ | 260/293.6 |
| 1,043,141 | 2/1970  | Germany .............. | 260/293.6 |
| 7,211,619 | 2/1973  | Netherlands .......... | 260/293.6 |
| 1,043,141 | 9/1966  | United Kingdom ...... | 260/293.6 |

Primary Examiner—Henry R. Jiles
Assistant Examiner—Robert T. Bond

Attorney, Agent, or Firm—Stevens, Davis, Miller & Mosher

[57] ABSTRACT

Novel N-substituted heterocyclic derivatives represented by the formula,

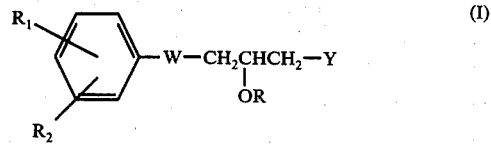

(I)

wherein R is hydrogen or lower alkanoyl; $R_1$ is hydrogen, lower alkyl, lower alkoxy, halogen, nitro, trifluoromethyl, amino or N-lower alkanoylamino; $R_2$ is hydrogen, halogen, amino or N-lower alkanoylamino; W is oxygen, sulfur, sulfinyl or sulfonyl; and Y is

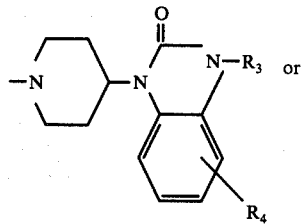 or

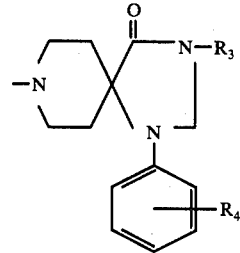

(wherein $R_3$ is hydrogen, lower alkyl or lower alkanoyl; and $R_4$ is hydrogen, halogen or lower alkyl), and pharmaceutically acceptable salts thereof, which have excellent anti-inflammatory, analgesic, sedative, anti-convulsive or anti-hypertensive activities.

2 Claims, No Drawings

N-SUBSTITUTED HETEROCYCLIC DERIVATIVES AND PREPARATION THEREOF

This is a continuation, of application Ser. No. 269,921, filed July 10, 1972, now abandoned.

The present invention relates to novel N-substituted heterocyclic derivatives, pharmaceutically acceptable salts thereof and preparation thereof. More particularly, the present invention pertains to novel N-substituted heterocyclic derivatives represented by the formula,

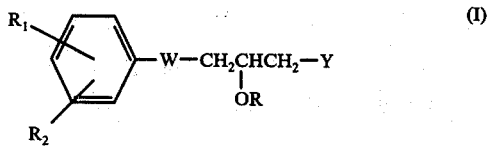

wherein R is hydrogen or lower alkanoyl; $R_1$ is hydrogen, lower alkyl, lower alkoxy, halogen, nitro, trifluoromethyl, amino or N-lower alkanoylamino; $R_2$ is hydrogen, halogen, amino or N-lower alkanoylamino; W is oxygen, sulfur, sulfinyl or sulfonyl; and Y is

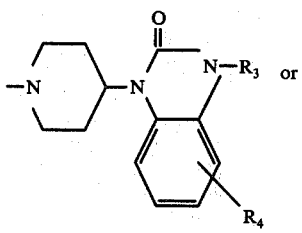

(wherein $R_3$ is hydrogen, lower alkyl or lower alkanoyl; $R_4$ is hydrogen, halogen or lower alkyl), and pharmaceutically acceptable acid addition salts thereof, and to a process for the preparation of the same.

As used herein, the term "lower alkyl", "lower alkoxy", and "lower alkanoyl" means such groups containing from one to seven carbon atoms which can be either straight or branched, and thus the lower-alkyl moiety represents, for example, methyl, ethyl, n-propyl, isopropyl, isobutyl, n-hexyl, and the like, and lower-alkanoyl represents, for example, formyl, acetyl, propionyl, and the like. The term "halogen" includes all four halogens, i.e., iodine, bromine, chlorine and fluorine.

The N-substituted heterocyclic derivatives of this invention form pharmaceutically acceptable salts with a variety of organic and inorganic acids. Such salts are formed with such acids as sulfuric, phosphoric, hydrochloric, hydrobromic, hydriodic, sulfamic, citric, lactic, maleic, malic, succinic, tartaric, cinnamic, acetic, benzoic, gluconic and ascorbic acids.

It has surprisingly been found by the present inventors that the compounds represented by the formula (I) above and their pharmaceutically acceptable salts have valuable pharmacological properties, in particular excellent anti-inflammatory, analgesic, sedative, anti-convulsive or anti-hypertensive activities.

Each of the pharmaceutically active compounds of this invention may be, e.g., incorporated, for oral administration, in a tablet as the sole active ingredient. A typical tablet is constituted by from 1 to 20 per cent binder, e.g. tragacanth; from 3 to 10 per cent lubricant, e.g. talcum; from 0.25 – 1.0 per cent lubricant, e.g. magnesium stearate; an average dose of active ingredient; and q.s. 100 per cent of filler, e.g. lactose. The usual oral dosage is 1 – 1000 mg per os daily.

Accordingly, an object of the present invention is to provide novel and useful N-substituted heterocyclic derivatives and salts thereof which have excellent pharmacological properties. Another object is to provide processes for producing such novel and useful N-substituted heterocyclic derivatives and salts thereof. A further object is to provide pharmaceutical composition containing such novel and useful N-substituted heterocyclic derivatives or salts thereof. Other objects and merits of the present invention will be apparent from the following descriptions.

In order to accomplish these objects, the present invention provides novel N-substituted heterocyclic derivatives represented by the formula (I) and acid addition salts thereof.

According to the present invention, the novel N-substituted heterocyclic derivatives represented by the formula (1) may be prepared by a variety of methods.

One method for producing the N-substituted heterocyclic derivatives of the formula (I) comprises reacting a compound represented by the formula, $$A - CH_2 - Z \qquad (II)$$

wherein A is

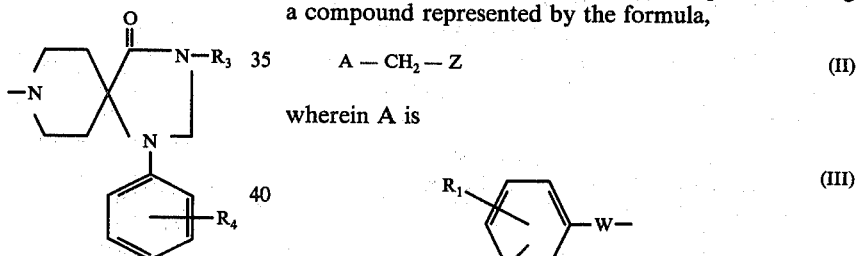

(wherein $R_1$, $R_2$ and W are as defined above) or a group of Y (wherein Y is as defined above) and Z is

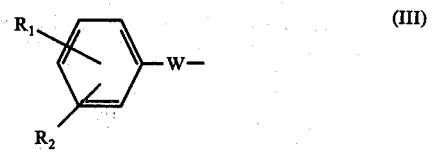

(wherein R is as defined above and X is halogen), with a compound represented by the formula, $$A' - H \qquad (IV)$$

wherein A' is a group of Y when A is a group of the formula (III) or a group of the formula (III) when A is a group of Y.

The reaction may generally be effected in an organic solvent or solvent mixture. Suitable solvents include methanol, ethanol, n-propanol, iso-propanol, n-butanol, benzene, toluene, xylene, dimethylformamide and the like, and a solvent mixture thereof. The reaction may be carried out at a temperature within a range between about room temperature and the boiling point of the solvent employed. When Z is

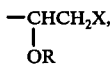

(wherein R and X are as defined above), the reaction may be preferably carried out in the presence of an acid acceptor to catch the acid which is liberated during the course of the reaction. Suitable acid acceptors include sodium carbonate, potassium carbonate, sodium bicarbonate, potassium bicarbonate, sodium hydroxide, potassium hydroxide, sodium hydride, potassium hydride, triethylamine and the like.

The compounds of the formula (I), wherein R is hydrogen, can also be prepared by treating a compound represented by the formula,

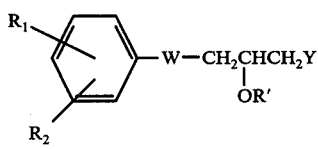

(V)

wherein $R_1$, $R_2$, W and Y are as defined above and R' is lower alkanoyl, with a saponifying agent. Suitable saponifying agents include sodium hydroxide, potassium hydroxide, sodium carbonate, potassium carbonate, sodium bicarbonate, potassium bicarbonate, hydrochloric acid, sulfuric acid and the like.

The hydrolysis is carried out at 10° to 60° C in the presence of a solvent such as water, methanol, ethanol, n-propanol, iso-propanol, n-butanol or a solvent mixture thereof.

The compounds of the formula (I), wherein R is lower alkanoyl, can also be prepared by treating a compound represented by the formula,

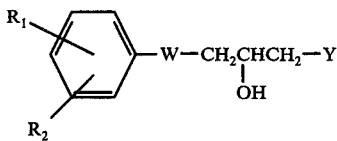

(VI)

wherein $R_1$, $R_2$, W and Y are as defined above, with a compound represented by the formula, (R'' — CO)$_2$O       (VII)

wherein R'' is lower alkyl.

The reaction may generally be effected at a temperature within a range between about room temperature and the boiling point of the solvent employed in an organic solvent or solvent mixture.

Suitable solvents include benzene, toluene, xylene, pyridine, acetic acid, dimethylformamide and the like, and a solvent mixture thereof.

The compounds of the formula (I), wherein R is hydrogen and W is oxygen or sulfur, can also be prepared from the corresponding compounds represented by the formula,

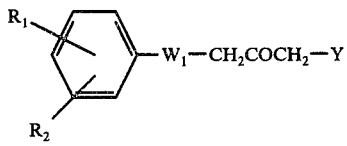

(VIII)

wherein $R_1$, $R_2$ and Y are as defined above and $W_1$ is oxygen or sulfur, by reduction. The compounds of the formula (VIII) can be reduced with a suitable reducing agent such as sodium in an alcoholic solvent, hydrogen in the presence of a catalyst, sodium borohydride or the like. The reaction is generally carried out in the presence of a solvent or solvent mixture. The choice of solvent depends on the reducing agent employed, and solvent is selected from a group consisting of water, ethanol, ether, tetrahydrofuran, dioxane, N-ethylmorpholine and the like. The reaction is carried out at room temperature, at a temperature below room temperature or at an elevated temperature.

The compounds of the formula (I) wherein W is sulfur can be converted to the compounds wherein W is sulfinyl or sulfonyl by treating such compounds with an oxidizing agent. As the oxidizing agent, there is used, for example, chromic acid, nitric acid, hydrogen peroxide, organic peracid (e.g. performic, peracetic, perbenzoic or m-chloroperbenzoic acid), sodium periodate, potassium periodate, persulfate, selenium dioxide, lead tetracetate, manganese dioxide or ruthenium tetroxide. The reaction is advantageously effected in the presence of a solvent, in general. The choice of the solvent depends on the oxidizing agent employed, and the solvent is selected from a group consisting of water, chloroform, carbon tetrachloride, acetone, acetic acid, formic acid, sulfuric acid, pyridine, dioxane, benzene, toluene, ether, ethyl acetate, methanol, ethanol and the like, and a mixture thereof. The reaction temperature varies depending on the oxidizing agent employed. Generally, the reaction proceeds readily at room temperature, but the temperature may be higher or lower, for example, 0° - about 100° C or the boiling point of the solvent employed, preferably 10° - 60° C, if necessary to effect the desired control of the reaction.

The thus obtained N-substituted heterocyclic derivatives of the formula (I) in free base form are converted to the acid-addition salt form by interaction of the base with an acid. In like manner, the free bases can be regenerated from the acid-addition salt form in a conventional manner, that is, by treating the salts with strong aqueous bases, for example, alkali metal hydroxides, alkali metal carbonates and alkali metal bicarbonates. The bases thus regenerated can then be interacted with the same or a different acid to give back the same or a different acid-addition salt. Thus the novel bases and all of their acid-addition salts are readily interconvertible.

According to the above processes, there are obtained, for example, the following N-substituted heterocyclic derivatives:

1-{1-[3-(p-Fluorophenylthio)-2-hydroxypropyl]-4-piperidyl}-2-oxobenzimidazoline

1-{1-[3-(p-Tolylthio)-2-hydroxypropyl]-4-piperidyl}-2-oxobenzimidazoline

1-{1-[3-(p-Tolyloxy)-2-hydroxypropyl]-4-piperidyl}-2-oxobenzimidazoline

1-{1-[3-(m-Trifluoromethylphenoxy)-2-hydroxypropyl]-4-piperidyl}-2-oxobenzimidazoline 1-{1-[3-(p-Chloro-m-tolyloxy)-2-hydroxypropyl]-4-piperidyl}-2-oxobenzimidazoline 1-{1-[3-(p-Fluorophenoxy)-2-hydroxypropyl]-4-piperidyl}-2-oxobenzimidazoline 1-{1-[3-(p-Tolylthio)-2-acetyloxypropyl]-4-piperidyl}-3-acetyl-2-oxobenzimidazoline 1-{1-[3-(p-Fluorophenylsulfinyl)-2-hydroxypropyl]-4-piperidyl}-2-oxobenzimidazoline 1-{1-[3-(p-Tolylsulfinyl)-2-hydroxypropyl]-4-piperidyl}-2-oxobenzimidazoline 1-{1-[3-(p-Fluorophenoxy)-2-acetyloxypropyl]-4-piperidyl}-2-oxobenzimidazoline 1-{1-[3-(p-Tolylthio)-2-hydroxypropyl]-4-piperidyl}-3-acetyl-2-oxobenzimidazoline 1-{1-[3-(p-Fluorophenoxy)-2-acetyloxypropyl]-4-piperidyl}-3-acetyl-2-oxobenzimidazoline 1-{1-[3-(p-Fluorophenoxy)-2-hydroxypropyl]-4-piperidyl}-3-acetyl-2-oxobenzimidazoline 1-{1-[3-(p-Methoxyphenoxy)-2-hydroxypropyl]-4-piperidyl}-2-oxobenzimidazoline 1-{1-[3-(p-Fluorophenoxy)-2-hydroxypropyl]-4-piperidyl}-3-methyl-2-oxobenzimidazoline 1-{1-[3-(p-Fluorophenylsulfonyl)-2-hydroxypropyl]-4-piperidyl}-2-oxobenzimidazoline 1-{1-[3-(p-Nitrophenoxy)-2-hydroxypropyl]-4-piperidyl}-2-oxobenzimidazoline 1-{1-[3-(o-Acetoamido-p-fluorophenoxy)-2-hydroxypropyl]-4-piperidyl}-2-oxobenzimidazoline 1-Phenyl-8-[3-(p-fluorophenoxy)-2-hydroxypropyl]-4-oxo-1,3,8-triazaspiro[4,5]decane 1-Phenyl-8-[3-(p-chloro-m-tolyloxy)-2-hydroxypropyl]-4-oxo-1,3,8-triazaspiro[4,5]decane 1-Phenyl-3-acetyl-8-[3-(p-fluorophenoxy)-2-acetyloxypropyl]-4-oxo-1,3,8-triazaspiro[4,5]decane 1-Phenyl-8-[3-(p-fluorophenylthio)-2-hydroxypropyl]-4-oxo-1,3,8-triazaspiro[4,5]decane 1-Phenyl-8-[3-(p-fluorophenylsulfinyl)-2-hydroxypropyl]-4-oxo-1,3,8-triazaspiro[4,5]decane 1-Phenyl-8-[3-(o-acetoamido-p-fluorophenoxy)-2-hydroxypropyl]-4-oxo-1,3,8-triazaspiro[4,5]decane The invention is further disclosed in the following Examples of more preferred embodiments thereof, which are presented for the purpose of illustration and it is not intended to limit the scope of the invention.

EXAMPLE 1

A mixture of 2.77 g of 1,2-epoxy-3-(p-fluorophenylthio)propane, 3.26 g of 1-(4-piperidyl)-2-oxobenzimidazoline and 50 ml of ethanol is refluxed for five hours.

The reaction mixture is concentrated under reduced pressure, and to the residue is added 100 ml of water. The precipitate formed is collected by filtration and dried to give 1-{1-[3-(p-fluorophenylthio)-2-hydroxypropyl]-4-piperidyl}-2-oxobenzimidazoline, m.p. 133° - 138° C. Recrystallization from benzene gives white crystals, m.p. 157° - 159° C.

The following compounds are obtained in the same manner as in Example 1:

1-{1-[3-(p-Tolylthio)-2-hydroxypropyl]-4-piperidyl}-2-oxobenzimidazoline, m.p. 155° - 157° C.

1-{1-[3-(p-Tolyloxy)-2-hydroxypropyl]-4-piperidyl}-2-oxobenzimidazoline, m.p. 163° - 164° C.

1-{1-[3-(m-Trifluoromethylphenoxy)-2-hydroxypropyl]-4-piperidyl}-2-oxobenzimidazoline, m.p. 195° - 196° C.

1-{1-[3-(p-Chloro-m-tolyloxy)-2-hydroxypropyl]-4-piperidyl}-2-oxobenzimidazoline, m.p. 210° - 211° C.

1-{1-[3-(p-Fluorophenoxy)-2-hydroxypropyl]-4-piperidyl}-2-oxobenzimidazoline, m.p. 177° - 178° C.

1-{1-[3-(p-Fluorophenylsufinyl)-2-hydroxypropyl]-4-piperidyl}-2-oxobenzimidazoline oxalate, m.p. 190° - 192° C (decomp.)

1-{1-[3-(p-Tolylsulfinyl)-2-hydroxypropyl]-4-piperidyl}-2-oxobenzimidazoline oxalate, m.p. 210° - 211° C (decomp.)

1-Phenyl-8-[3-(p-fluorophenoxy)-2-hydroxypropyl]-4-oxo-1,3,8-triazaspiro[4,5]decane, m.p. 164° - 166° C.

1-Phenyl-8-[3-(p-chloro-m-tolyloxy)-2-hydroxypropyl]-4-oxo-1,3,8-triazaspiro[4,5]decane, m.p. 156° - 158° C.

EXAMPLE 2

A mixture of 2.2 g of 1-{1-[3-(p-fluorophenoxy)-2-acetyloxypropyl]-4-piperidyl}-2-oxobenzimidazoline, 1.1 g of potassium hydroxide, 5 ml of water and 20 ml of ethanol is stirred at room temperature for one hour. The reaction mixture is poured into 200 ml of water. After cooling, the precipitate formed is collected by filtration and dried to give 1-{1-[3-(p-fluorophenoxy)-2-hydroxypropyl]-4-piperidyl}-2-oxobenzimidazoline, m.p. 175° - 176° C. Recrystallization from benzene gives white crystals, m.p. 177° - 178° C.

EXAMPLE 3

A mixture of 2.2 g of 1-{1-[3-(p-tolylthio)-2-hydroxypropyl]-4-piperidyl}-3-acetyl-2-oxobenzimidazoline, 5.1 g of acetic anhydride and 30 ml of pyridine is heated at 80° C for 2 hours. After the reaction mixture has been cooled, a mixture of 100 ml of chloroform and 150 ml of water is added thereto. The aqueous layer is separated and extracted with chloroform. The organic layers are combined, washed with water, dried over sodium sulfate and evaporated under reduced pressure. The oily residue is dissolved in iso-propanol and to this solution is added a warm solution of 0.55 g of oxalic acid in iso-propanol. After cooling, the precipitated oxalate is collected by filtration and dried to give 1-{1-[3-(p-tolylthio)-2-acetyloxypropyl]-4-piperidyl}-3-acetyl-2-oxobenzimidazoline oxalate, m.p. 197° - 198° C (decomp.). Recrystallization from ethanol gives white crystals, m.p. 199° - 200° C (decomp.).

EXAMPLE 4

To a mixture of 0.2 g of sodium borohydride in 10 ml of ethanol is added dropwise a solution of 2 g of 1-phenyl-8-[3-(p-fluorophenoxy)-2-oxopropyl]-4-oxo-1,3,8-triazaspiro[4,5]decane in 20 ml of ethanol. The mixture is stirred at room temperature for five hours. The resulting mixture is decomposed with 2N hydrochloric acid, diluted with water, made alkaline with sodium hydroxide and diluted again with water. After cooling, the precipitate is collected by filtration and dried to give 1-phenyl-8-[3-(p-fluorophenoxy)-2-hydroxypropyl]-4-oxo-1,3,8-triazaspiro[4,5]decane, m.p. 152° - 154° C. Recrystallization from iso-propanol gives pale yellow crystals, m.p. 164° - 166° C.

Example 5

To a solution of 1 g of 1-{1-[3-(p-fluorophenylthio)-2-hydroxypropyl]-4-piperidyl}-2-oxo-benzimidazoline in 20 ml of glacial acetic acid is added dropwise 0.6 g of 35% aqueous hydrogen peroxide under cooling. The mixture is stirred for one hour at a temperature of 20° - 30° C. Then the reaction mixture is poured into 50 ml of water, neutralized with aqueous ammonia and extracted with chloroform. The organic layer is washed with water, dried over sodium sulfate and evaporated under reduced pressure.

The oily residue is dissolved in iso-propanol and to this solution is added a warm solution of 0.25 g of oxalic acid in iso-propanol. After cooling, the precipitated oxalate is collected by filtration and dried to give 1-{1-[3-(p-fluorophenylsulfinyl)-2-hydroxypropyl]-4-piperidyl}-2-oxobenzimidazoline oxalate, m.p. 180° - 190° C (decomp.). Recrystallization from ethanol gives white powders, m.p. 190° - 192° C (decomp.).

What is claimed:

1. A chemical compound selected from the group consisting of a benzimidazoline derivative having the formula:

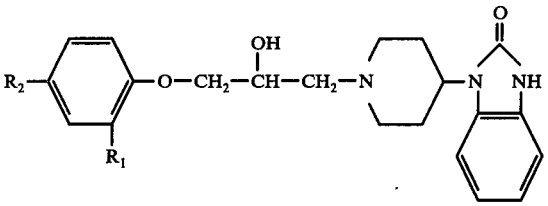

and the therapeutically active acid addition salts thereof, wherein $R_1$ is a member selected from the group consisting of hydrogen, halo, and loweralkoxy; and $R_2$ is a member selected from the group consisting of hydrogen and halo.

2. 1-{1-[3-p-Fluorophenoxy-2-hydroxypropyl]-4-piperidyl}-2-oxobenzimidazoline.

* * * * *